United States Patent
Nie et al.

(10) Patent No.: US 11,175,226 B2
(45) Date of Patent: Nov. 16, 2021

(54) DEVICE AND METHOD FOR DETECTING FLUID TRANSPARENCY

(71) Applicant: FATRI UNITED TESTING & CONTROL (QUANZHOU) TECHNOLOGIES CO., LTD., Fujian (CN)

(72) Inventors: Yongzhong Nie, Fujian (CN); Zhongping Zhang, Fujian (CN)

(73) Assignee: FATRI UNITED TESTING & CONTROL (QUANZHOU) TECHNOLOGIES CO., LTD., Quanzhou (CN)

( * ) Notice: Subject to any disclaimer, the term of this patent is extended or adjusted under 35 U.S.C. 154(b) by 0 days.

(21) Appl. No.: 16/487,927

(22) PCT Filed: Nov. 30, 2018

(86) PCT No.: PCT/CN2018/118695
§ 371 (c)(1),
(2) Date: Aug. 22, 2019

(87) PCT Pub. No.: WO2019/109871
PCT Pub. Date: Jun. 13, 2019

(65) Prior Publication Data
US 2020/0340916 A1 Oct. 29, 2020

(30) Foreign Application Priority Data
Dec. 5, 2017 (CN) .......................... 201711268447.7

(51) Int. Cl.
*G01N 21/59* (2006.01)
*G01N 21/47* (2006.01)

(52) U.S. Cl.
CPC ............. *G01N 21/59* (2013.01); *G01N 21/47* (2013.01); *G01N 2201/025* (2013.01); *G01N 2201/06113* (2013.01)

(58) Field of Classification Search
CPC ........ G01N 21/59; G01N 21/47; G01N 21/51; G01N 2201/025; G01N 2201/06113;
(Continued)

(56) References Cited

U.S. PATENT DOCUMENTS 2,316,239 A * 4/1943 Hare ..................... F16L 55/00
250/394
4,725,140 A * 2/1988 Musha ................... G01N 21/21
356/336
(Continued)

FOREIGN PATENT DOCUMENTS

CN 102128814 7/2011
CN 104020130 9/2014
(Continued)

OTHER PUBLICATIONS

International Search Report for International Application PCT/CN2018/118695, dated Feb. 27, 2019.
(Continued)

*Primary Examiner* — Tri T Ton
(74) *Attorney, Agent, or Firm* — Burris Law, PLLC

(57) ABSTRACT

The present invention discloses a device and method for detecting fluid transparency. The detection device comprises: a detection pipeline, which allows a beam to be incident on and emergent from a fluid therein; a laser tube, used for outputting the incident beam; and a photoelectric detector, used for detecting the emergent beam from the fluid, wherein the photoelectric detector comprises a scatter detector and a transmission detector; and the detection method comprises obtaining a scattered background noise
(Continued)

value and a transmission background noise value of a device, obtaining the scattered light intensity $I_{scatter}$ obtained by the scatter detector and the transmission light intensity $I_{transmission}$ obtained by the transmission detector, and calculating the particle-absorbed light intensity $I_{absorb}$; obtaining the total light intensity $I_{total}$ of a laser; and obtaining a fluid transparency T. With the described detection device and detection method, the accuracy of detecting fluid transparency may be effectively improved.

14 Claims, 1 Drawing Sheet

(58) Field of Classification Search
CPC ........... G01N 15/0211; G01N 15/1459; G01N 2015/0053; G01N 21/31; G01N 21/532; G01N 33/2858; G01N 33/2888
USPC .................................................. 356/432–448
See application file for complete search history.

(56) References Cited

U.S. PATENT DOCUMENTS

| | | | |
|---|---|---|---|
| 6,388,752 B1* | 5/2002 | Ziegler | ................ G01N 21/532 356/342 |
| 2010/0044586 A1* | 2/2010 | Duhr | .................. G01N 21/6428 250/459.1 |
| 2011/0255076 A1 | 10/2011 | Melcher | |

FOREIGN PATENT DOCUMENTS

| | | |
|---|---|---|
| CN | 105300929 A | 2/2016 |
| CN | 107831143 | 3/2018 |
| CN | 207457010 | 6/2018 |
| JP | H04372861 | 12/1992 |

OTHER PUBLICATIONS

Office Action issued to Chinese counterpart application No. 201711268447.7 dated Mar. 13, 2019.
Office Action issued to Chinese counterpart application No. 201711268447.7 dated Jun. 20, 2019.
Third Office Action of counterpart Chinese application No. 201711268447.7 dated Oct. 21, 2019.

* cited by examiner

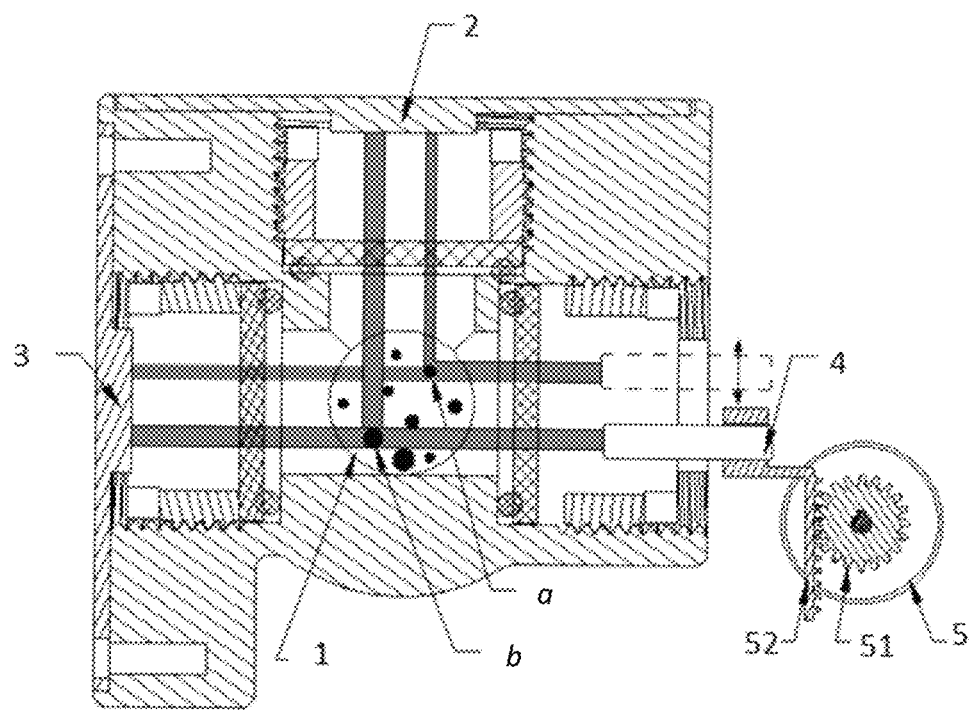

DEVICE AND METHOD FOR DETECTING FLUID TRANSPARENCY

CROSS-REFERENCE TO RELATED APPLICATIONS

This application is a U.S. national phase application of International Application No. PCT/CN2018/118695, filed on Nov. 30, 2018, which claims priority to and the benefit of Chinese Patent Application No. 201711268447.7, filed on Dec. 5, 2017. The disclosures of the above applications are incorporated herein by reference.

FIELD

The present disclosure relates to the technical field of detection device, in particular to a fluid transparency detection device and a method for detecting by using the device.

BACKGROUND

The statements in this section merely provide background information related to the present disclosure and may not constitute prior art.

In order to reduce wear loss during operation of engine, bearing, gear and so on, it is often necessary to equip lubricating oil system, but factors such as impurities and debris in lubricating oil will bring great disaster. Failure in operation of large-scale mechanical equipment is often due to a vicious cycle caused by the accumulation of abrasive debris in lubricating oil. In a wear failure diagnosis system, there is a strong correlation between the degree of damage to wear components (such as engines, rolling bearings, gears, etc.) and particles in the lubrication system. In order to realize the detection of lubricating oil particles, a particle morphology detection device, such as a fluid transparency detection device, is usually installed in a lubricating oil pipeline at first to monitor the lubricating oil quality on line in real time, and provide an effective basis for the failure diagnosis of an engine, a bearing, a gear and the like, thereby quickly and accurately figuring out the abrasion state and the failure reason of the equipment.

In the conventional liquid particle detection method, a laser beam is guided to irradiate a transparent device filled with the liquid, and particles in the liquid are detected by measuring scattered light intensity. This method has the following disadvantages: (1) the scattered light is obtained in a single mode, and the total light intensity scattered in all the directions cannot be accurately obtained, resulting a low accuracy in obtaining the total light intensity; (2) a method for calculating air transparency is directly applied to the calculation of fluid transparency without considering the inherent influencing impurities of the fluid, namely the background noise value of the pure fluid; both of these aspects result in an influence on the accuracy of the fluid transparency calculation.

SUMMARY

In order to overcome the defects of the prior art, the technical problems to be solved by the invention are: (1) a detection device capable of more accurately measuring fluid transparency through detection of scattered and transmission light intensity; and (2) a method for detecting by using the device, so as to improve accuracy of the transparency detection.

In order to solve the first technical problem and achieve the technical object, the technical solution adopted by the invention is as follows:

A fluid transparency detection device, comprising: a detection pipeline which allows light beams to be incident on and emergent from a fluid in the pipeline; a laser tube used for outputting the incident light beam; a photoelectric detector used for detecting the emergent light beam from the fluid; wherein the photoelectric detector comprises a scatter detector and a transmission detector.

In the prior art, always a laser beam is guided to irradiate a transparent device filled with the liquid, and particles in the liquid are detected by measuring scattered light intensity, which leads to the disadvantages mentioned above in the background art. Therefore, the inventor creatively proposes a technical solution that the transmission detector and the scatter detector are simultaneously arranged in the device, which can effectively solve the technical problem, and the transmission light intensity after the liquid is transmitted can be obtained while the scattered light is obtained; the total light intensity is obtained by obtaining the transmission and scattered light intensity and particle-absorbed light intensity, so that the fluid transparency is more accurately obtained.

It should be noted that this patent takes lubricating oil as one of the applicable scenarios of the fluid to illustrate, which does not means that the device and method are only applicable to the application scenario in which lubricating oil is used, but that other fluids are also applicable.

It should be noted that the scatter detector is primarily used to obtain scattered light information of the laser tube.

It should be noted that the transmission detector is mainly used for obtaining the transmission intensity of the laser tube.

Preferably, the scatter detector is positioned out of the straight line with the beam output from the laser tube.

The scatter detector is used to identify the size and shape of particles. In a preferred embodiment, the scatter detector is positioned out of the straight line with the beam output from the laser tube, because if the scatter detector is positioned in the same straight line with the beam output from the laser tube, the scatter detector is low in sensitivity to receive the beam and is easily disturbed by the direct beam. Instead of being positioned in the same straight line, interference of light beams can be reduced, thus rendering a more accurate detection of the scattered light beam.

More preferably, the scatter detector is arranged in a plane perpendicular to the beam output from the laser tube, and the scatter detector, the detection pipeline and the laser tube, with each as a vertex, form a right-angle shape.

An experiment shows that the interference of the direct beam can be avoided to a greater extent by setting the above-mentioned position relation, and the scattered beam can be detected accurately.

Preferably, the transmission detector is arranged in the same straight line with the beam output from the laser tube, and the detection pipeline is arranged between the transmission detector and the laser tube.

Preferably, the detection device further comprises a drive unit for driving the laser tube to move.

In the existing fluid transparency detecting devices, the laser tube is fixed, and the output light beam is fixed at a certain position, therefore the detected particles are only limited to this position. Due to the fact that the masses of the particles are different, the particles can form layering in the fluid according to their masses, the existing devices may be limited in a narrow detection range, with relatively partial particles detected, so that the detected fluid transparency is not accurate enough. Therefore, the inventor creatively proposes that the laser tube fixed before is arranged to be movable, and the drive unit is used for driving the laser tube to move, so that the output light beam from the laser tube can cover the detection pipeline, the particles flowing through the whole detection pipeline are all detected, the obtained light intensity is more accurate, and the technical effect of improving the detection accuracy is further achieved.

Alternatively still, in another embodiment, after a measurement has been made by fixing the laser, the laser tube may be moved in the next measurement to conduct the measurement in another layer. That is, in this preferred embodiment, instead of being moved in once measurement, the laser tube is fixed in a measurement and moved after this, and the measurement of transparency is continued with the laser tube being fixed in another measurement. Finally, each of the measurement results is recorded, and the final measurement result is obtained through weighted averaging, so that the measurement result is more accurate.

Preferably, the drive unit is an electric motor.

As one embodiment, an electric motor may be provided in the detection device for driving the laser tube to move, resulting in movement of the output incident light beam.

More preferably, the movement of the laser tube is a lead screw movement or a gear movement.

The lead screw movement means that, in one embodiment, a nut is provided on the laser and the electric motor drives the screw matching the nut, thereby realizing movement.

The gear movement means that the electric motor and the laser tube are both provided with gear-shaped structural parts which are mutually matched to realize movement.

Preferably, the movement range of the laser tube is the diameter of the cross section of the detection pipeline.

Defining the movement range of the laser tube as the diameter of the cross section of the detection pipeline can ensure that the detection pipeline can be covered to a greater extent, the fluid in the pipeline can be fully covered by the light beam, so that a full detection of particles in each layer is achieved, and the detection accuracy is improved.

Preferably, the movement of the laser tube is at a constant velocity.

In the process of movement at a constant velocity, the signal of the sampled particle is relatively stable, so that the accuracy of detection and analysis results is higher.

In order to solve the second technical problem and achieve the technical object, the technical solution adopted by the invention is as follows:

A method for detecting fluid transparency using the device as described above, the method comprising the steps of:

S1: introducing pure fluid into the device, obtaining a scattered background noise value and a transmission background noise value of the device, and converting the scattered background noise value and the transmission background noise value correspondingly into a scattered light intensity background noise value $I_{scattered\ background\ noise}$ and a transmission light intensity background noise value $I_{transmission\ background\ noise}$;

S2: introducing a fluid to be detected into the device, outputting a laser beam by a laser tube, respectively obtaining scattered light and transmitted light voltage signals obtained by a scatter detector and a transmission detector, converting to obtain a scattered light intensity $I_{scatter}$ obtained by the scatter detector, a transmission light intensity $I_{transmission}$ obtained by the scatter detector, and a particle-absorbed light intensity $I_{absorb}$;

S3: outputting a total laser light intensity $I_{total\ light\ intensity}$ according to the result obtained in S2, wherein the calculation formula of the total laser light intensity is as follows:

$$I_{total\ light\ intensity} = I_{scatter} + I_{transmission} + I_{absorb} - I_{scattered\ background\ noise} - I_{transmission\ background\ noise};$$

S4: outputting a fluid transparency T according to the $I_{total\ light\ intensity}$ obtained in S3 and the $I_{transmission}$, wherein the calculation formula of the fluid transparency T is as follows:

$$T = (I_{transmission} - I_{transmission\ background\ noise}) / I_{total\ light\ intensity} \times 100\%.$$

It is to be noted that the existing method for measuring the transparency of a fluid usually directly obtains the values of the total laser light intensity and the transmission light intensity, and then directly divides the later by the former to obtain the transparency of the fluid. However, the total light intensity in the method is not easy to obtain and the accuracy of this direct division method is not enough, therefore, the inventor creatively proposes multiple steps to obtain the total light intensity, namely to respectively obtain the scattered light intensity, the transmission light intensity and the particle-absorbed light intensity of the laser, and then the total light intensity is obtained by adding the scattered light intensity, the transmission light intensity and the particle-absorbed light intensity. On the other hand, the method is generally applied to air measurement, but there are more impurities affecting scattering and transmission in the fluid than in the air, so the method of calculating air transparency cannot be simply directly applied to the calculation of fluid transparency. According to the method of the present invention, the detection accuracy of the total light intensity can be improved, so that the calculation accuracy of the transparency is improved.

Preferably, the laser tube in S2 is movable;

More preferably, the laser tube is moving during detection;

More preferably, the laser tube is moving prior to the detection process.

The laser tube is movable, and two preferable solutions can be adopted to render beneficial effects that the laser is not limited to a certain point or layer and is incident into the detection pipeline, so that the accuracy of each light intensity obtained by the detector can be improved.

Wherein, moving in the detection process refers to the movement in the process of obtaining the signals in S2, namely multiple layers of particles possibly formed in the pipeline can be detected in real time, the particle morphology of each layer is detected in the obtaining process, and the accuracy of the signals is improved.

In addition, moving prior to the detection process means that the laser tube is fixed in the process of obtaining the signals in S2, the detection is carried out in one layer of particles, and the laser tube is moved before the next detection is started, and then the morphology of the particles in another layer is detected. In this way, a higher signal accuracy can be obtained by weighted averaging multiple detection results.

Preferably, the S3 further comprises a follow-up step of: repeating S2 and S3 to obtain the maximum value $I_{max}$ of the total laser light intensity in a certain time; at this time, the fluid transparency $T = (I_{transmission} - I_{transmission\ background\ noise}) / I_{max} \times 100\%$.

It should be noted that in the actual use process of lubricating oil, due to a series of factors such as data obtaining accuracy, lubricating oil flow velocity and the like, the light intensity selected for the first time is not necessarily the accurate one. In order to avoid the calculation error of the total light intensity, the total light intensity is calculated each time during calculation and compared with the previous total light intensity, and the maximum total light intensity in a certain time is selected as the actual total light intensity, so that the measured total light intensity is closer to the actual total light intensity, and the detection result is more accurate.

Compared with the prior art, the invention has the following advantages:

1. The fluid transparency detection device of present invention is simultaneously provided with a scatter detector and a transmission detector; these two simultaneously provided photoelectric detectors can detect two data simultaneously in one device, the transparency of the fluid in the detection pipeline can be further detected, and the detection efficiency is improved, namely the transmission light intensity can be obtained after the light is transmitted from the liquid while the scattered light intensity is obtained; the detection accuracy of transparency is improved;

2. In the fluid transparency detection device of present invention, the laser tube is arranged to be movable, so that the output light beam from the laser tube can cover the detection pipeline, particles flowing through the whole detection pipeline are detected, and the technical effect of improving detection accuracy is further achieved;

3. The fluid transparency detection device of present invention preferably further comprises an electric motor, and the electric motor is connected with the laser tube so as to drive the laser tube to move, and the laser tube can be moved;

4. In the fluid transparency detection device of present invention, the movement range of the laser tube is set as the diameter of the cross section of the detection pipeline, the detection pipeline can be covered to a greater extent, so that the fluid in the pipeline can be fully covered by a light beam, a full detection of particles in each layer is achieved, and the detection accuracy is improved;

5. In the fluid transparency detection device of present invention, the laser tube moves at a constant speed, the signal of the sampled particle is stable in the process of the constant speed movement, and the accuracy of detection and analysis results is higher;

6. In the fluid transparency detecting method of present invention, the background noise values of scatter and transmission in the pure fluid are measured firstly, the inherent condition in the fluid is measured to serve as a comparison for subsequent measurement, thereby the accuracy of subsequent measurement is improved;

7. In the fluid transparency detecting method of present invention, the total light intensity is obtained in multiple steps, namely the scattered light intensity, the transmission light intensity and the particle-absorbed light intensity of laser light are respectively obtained, and then the total light intensity is obtained by adding these three values and denoising. According to the method, the detection accuracy of the total light intensity can be improved, so that the calculation accuracy of transparency is improved;

8. In the fluid transparency detecting method of present invention, by repeating S2 and S3 to obtain the maximum value Imax of the total laser light intensity in a certain time as the total light intensity, thus the measured total light intensity is more accurate.

The above description is merely a summary of the technical solutions of the present invention, in order to render a more clear understanding of the technical means of the present invention to implement according to the content of the description, and in order to render the above and other objects, features and advantages of the present invention to be more readily understood, the following detailed description of the preferred embodiments is carried out taken in conjunction with the accompanying drawings.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which:

FIG. 1 is a schematic view showing the structure of a preferred embodiment of the fluid transparency detection device of the present invention;

Wherein each reference numeral represents: 1. detection pipeline; 2. scatter detector; 3. transmission detector; 4. laser tube; 5. electric motor; 51. gear; 52. rack; a. particle; b. particle.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

In order to further illustrate the technical means of the present invention for achieving the intended purposes thereof as well as effects, the following detailed description is made, taken in conjunction with the accompanying drawings and preferred embodiments, to illustrate specific embodiments, structures, features and efficacy thereof according to the present invention.

Embodiment 1 (Fluid Transparency Detection Device)

FIG. 1 is a schematic view showing the structure of a preferred embodiment of the fluid transparency detection device of the present invention, comprising: a detection pipeline 1 which allows a light beam to be incident on and emergent from a fluid in the pipe; a laser tube 4 for outputting the incident light beam; and a photoelectric detector for detecting the emergent light beam from the fluid.

The photoelectric detector includes: a scatter detector 2 for detecting a scattered light beam; a transmission detector 3 for detecting a transmission light beam; the scatter detector is arranged in a plane perpendicular to the beam output from the laser tube, and the scatter detector, the detection pipeline and the laser tube, with each as a vertex, form a right-angle shape; the transmission detector is arranged in the same straight line with the beam output from the laser tube, and the detection pipeline is arranged between the transmission detector and the laser tube.

The detection device further comprises an electric motor 5 serving as a drive unit, and the electric motor is connected with the laser tube to drive the laser tube to move. The electric motor drives the laser tube to move by means of the gear 51 and the rack 52.

The specific working process of the detection device is as follows: When the device is started, the laser tube is controlled to irradiate at the liquid at the lowest end of a travel and at the lowest layer of the detection pipeline by the electric motor, the gear and the rack, and the distribution condition of particles at the lowest layer is analyzed; and then the electric motor driving program is controlled to move the laser tube at a constant speed, so that the laser moves while scanning in the pipeline, the output signal of the photoelectric detector is collected simultaneously, the condition of particles at different layers in the pipeline is analyzed, and then a dynamic analysis of the distribution of the particles in the pipeline is realized. For particles with different sizes, such as relatively small particles a and relatively large particles b in the FIGURE, due to the fact that the particles are layered according to different masses, a light beam can be movably incident in and cover the fluid in the detection pipeline by means of the device, different particles produce different scatter and transmission, thus the detection result of the photoelectric detector is more comprehensive and accurate, and the detection accuracy is improved for detecting the transparency and the particle concentration of the fluid.

In this embodiment, the photoelectric detector comprises a scatter detector and a transmission detector; these two simultaneously provided photoelectric detectors can detect two data simultaneously in one device, the transparency of the fluid in the detection pipeline can be further detected, and the detection efficiency is improved, namely the transmission light intensity can be obtained after the light is transmitted from the liquid while the scattered light intensity is obtained; the detection accuracy of transparency is improved.

In this embodiment, the scatter detector is arranged at the plane perpendicular to the laser tube, and the scatter detector, the detection pipeline and the laser tube, with each as a vertex, form a right-angle shape, in order to reduce interference of light beams and enable scattered light beam detection to be more accurate. In other preferred embodiments, the scatter detector is positioned out of the straight line with the beam output from the laser tube, which can also achieve the above technical effect.

In the embodiment, the laser tube is arranged to be movable, so that the output light beam from the laser tube can cover the detection pipeline, particles flowing through the whole detection pipeline are detected, and the technical effect of improving detection accuracy is further achieved.

In the present embodiment, the movement of the laser tube is gear movement, and in other embodiments, the movement may be lead screw movement or the like.

In this embodiment, the movement range of the laser tube is the diameter of the cross section of the detection pipeline. the movement range of the laser tube is set as the diameter of the cross section of the detection pipeline, the detection pipeline can be covered to a greater extent, so that the fluid in the pipeline can be fully covered by a light beam, a full detection of particles in each layer is achieved, and the detection accuracy is improved. In other embodiments, the movement range of may vary from case to case and is not limited to the preferred embodiment of the present embodiment.

In this embodiment, the movement of the laser tube is at a constant speed. The signal of the sampled particle is stable in the process of the constant speed movement, and the accuracy of detection and analysis results is higher.

Embodiment 2 (A Method for Detecting Fluid Transparency)

This embodiment is a first preferred embodiment of the method for detecting the transparency of a fluid using the device as described above, the method comprising the steps of:

S1: introducing pure fluid into the device, obtaining a scattered background noise value and a transmission background noise value of the device, and converting the scattered background noise value and the transmission background noise value correspondingly into a scattered light intensity background noise value $I_{scattered\ background\ noise}$ and a transmission light intensity background noise value $I_{transmission\ background\ noise}$;

S2: introducing a fluid to be detected into the device, outputting a laser beam by a laser tube, respectively obtaining scattered light and transmitted light voltage signals obtained by a scatter detector and a transmission detector, converting to obtain a scattered light intensity $I_{scatter}$ obtained by the scatter detector, a transmission light intensity $I_{transmission}$ obtained by the scatter detector, and then obtaining a particle-absorbed light intensity $I_{absorb}$;

S3: outputting a total laser light intensity $I_{total\ light\ intensity}$ according to the result obtained in S2, wherein the calculation formula of the total laser light intensity is as follows: $I_{total\ light\ intensity} = I_{scatter} + I_{transmission} + I_{absorb} - I_{scattered\ background\ noise} - I_{transmission\ background\ noise}$;

S4: outputting a fluid transparency T according to the $I_{total\ light\ intensity}$ obtained in S3 and the $I_{transmission}$, wherein the calculation formula of the fluid transparency T is as follows:

$$T = (I_{transmission} - I_{transmission\ background\ noise}) / I_{total\ light\ intensity} \times 100\%;$$

Specifically, in the process of analyzing the transparency of the lubricating oil, firstly, the background noise values in the pure fluid are measured, so that the inherent factors influencing the measurement parameters in the fluid are removed. And then the scattered light intensity $I_{scatter}$ and the transmission light intensity $I_{transmission}$ are respectively obtained by the scatter detector and the transmission detector. By means of an optical signal conditioning circuit, weak light intensity can be converted into voltage pulse signals; the processed scattered light signal contains information related to the number and size of particles in lubricating oil; and the processed transmitted light signal contains the transmission light intensity of the lubricating oil. According to structural design and circuit conversion, the voltage signal $U_{transmission}$ through the lubricating oil can be received at the transmission detector, and the amplitude of the signal represents the light intensity. In the optical granularity analysis, the scattered light intensity voltage signal $U_{scatter}$ is obtained.

Through the above steps, voltage signal $U_{scatter}$ of the scattered light intensity of the particle can be obtained, the size of the particle can be calculated, voltage signal $U_{absorb}$ of the light intensity absorbed by the particle can be obtained through analyzing the absorption coefficient of the particle, and a certain proportional relationship exists between $U_{absorb}$ and $U_{scatter}$, that is: $U_{absorb} = k \times U_{scatter}$. Wherein, K is related to the material of the particle, the absorption coefficient and the like, can be corrected, and is determined through calibration in practice.

The scattered light intensity $I_{scatter}$, the transmission light intensity $I_{transmission}$ and particle-absorbed light intensity $I_{absorb}$ are then obtained respectively according to the voltage signals. And then the total light intensity $I_{total\ light\ intensity}$ in measurement is obtained by adding these three intensity values and subtracting the inherent background noise value of the pure fluid.

The total light intensity is obtained in multiple steps, namely the scattered light intensity, the transmission light intensity and the particle-absorbed light intensity of laser light are respectively obtained, and then the total light intensity is obtained by adding these three values minus the background noise values. According to this method, the detection accuracy of the total light intensity can be improved, so that the calculation accuracy of transparency is improved.

Embodiment 3 (A Method for Detecting Fluid Transparency)

This embodiment, which is a second preferred embodiment of the fluid transparency detection method of the present invention, differs from the above-mentioned embodiment 2 in that: the laser tube in S2 is movable. The laser tube is movable, and the laser is not limited to a certain point or layer to be incident into the detection pipeline, so that the accuracy of each light intensity obtained by the detector is improved.

In addition, laser tube movement has another further benefit. In another preferred embodiment, after a measurement has been made by fixing the laser, the laser tube may be moved in the next measurement to conduct the measurement in another layer. That is, in this preferred embodiment, instead of being moved in once measurement, the laser tube is fixed in a measurement and moved after this, and the measurement of transparency is continued with the laser tube being fixed in another measurement. Finally, each of the measurement results is recorded, and the final measurement result is obtained through weighted averaging, so that the measurement result is more accurate.

The specific steps are as follows:

(1) Initially, when the laser lamp is controlled to be positioned at the bottom most layer of the travel (the bottom most layer within a range of the diameter of the cross section of the detection pipeline), the photoelectric detector is sampled, meanwhile, particles and transparency of the lubricating oil are analyzed, and the analysis result $x_0$ corresponding to the current position is recorded.

(2) The laser tube is controlled to move upwards at a constant speed, the photoelectric detector is sampled, meanwhile, particles and transparency of the lubricating oil are analyzed, and the analysis result $x_i$ corresponding to the current position is recorded.

(3) When the laser tube moves to the highest layer of the travel (the uppermost layer in a range of the diameter of the cross section of the detection pipeline), the photoelectric detector is sampled, meanwhile, particles and transparency of the lubricating oil are analyzed, and the analysis result $$\frac{x_{max}}{2}-1$$

corresponding to the current position is recorded.

(4) The laser tube is controlled to move downwards at a constant speed, the photoelectric detector is sampled, meanwhile, particles and transparency of the lubricating oil are analyzed, and the analysis result $$\frac{x_{max}}{2}+i$$

corresponding to the current position is recorded.

(5) Similarly, when the laser tube moves to the initial position of the travel, the analysis result $x_{max-1}$ is obtained, and the first round of layered analysis is finished.

(6) A secondary analysis on the result of the entire first round of layered analysis is performed to obtain the particle distribution and the fluid transparency in the whole pipeline. It is considered herein that the form of the fluid in the tube does not change much in a short time, and the movement of the laser tube is a relatively back-and-forth movement at a constant speed, so the results of back-and-forth layered scanning are considered to be consistent, and the results are averaged to obtain the distribution of the particles at each place and the transparency in the fluid.

$$x_i = \frac{x_i + x_{max-i-1}}{2}$$

Others in the embodiment are the same as in Embodiment 2 described above and thus will not be repeated herein.

Embodiment 4 (A Method for Detecting Fluid Transparency)

The present embodiment, which is a third preferred embodiment of the fluid transparency detection method of the present invention, differs from the above-mentioned Embodiment 2 in that the S3 further comprises the step of repeating S2 and S3 to obtain the maximum value of the total laser light intensity in a certain time $I_{max}$; and then the fluid transparency $T = (I_{transmission} - I_{transmission\ background\ noise})/I_{total\ light\ intensity} \times 100\%$.

In the actual use process of lubricating oil, due to a series of issues such as data obtaining accuracy, lubricating oil flow velocity and the like, the light intensity selected for the first time is not necessarily the accurate one. In order to avoid the calculation error of the total light intensity, the total light intensity is calculated each time during calculation, and compared with the previous total light intensity, the maximum total light intensity in a certain time is selected as the actual total light intensity, so that the measured total light intensity is closer to the actual total light intensity, and the detection result is more accurate.

The selection of the total light intensity is a repetitive operation, and in calculation, the selected total light intensity is compared with the last total light intensity. From the beginning, only the maximum total light intensity is selected, so only once calculation of the total light intensity is carried out in each measurement, and the maximum total light intensity can be obtained through once comparison.

Others in the embodiment are the same as those of Embodiments 2 and 3 described above and will not be repeated herein.

Embodiment 5 (A Device for Detecting Fluid Transparency)

The basic structure of the embodiment is as follows: A particle morphology detection device, comprising: a detection pipeline which allows light beams to be incident on and emergent from a fluid in the pipeline; a laser tube used for outputting the incident light beam; a photoelectric detector used for detecting the emergent light beam from the fluid; the detection device further comprising a drive unit for driving the laser tube to move.

In addition to the basic structure described above, the following preferred embodiments may be included:

Preferably, the drive unit is an electric motor.

Preferably, the movement of the laser tube is a lead screw movement or a gear movement.

Preferably, the movement range of the laser tube is the diameter of the cross section of the detection pipeline.

Preferably, the movement of the laser tube is at a constant speed.

Preferably, the photoelectric detector comprises a scatter detector.

Preferably, the scatter detector is positioned out of the straight line with the beam output from the laser tube.

Preferably, the scatter detector is arranged in a plane perpendicular to the beam output from the laser tube, and the scatter detector, the detection pipeline and the laser tube, with each as a vertex, form a right-angle shape.

Preferably, the photoelectric detector further comprises a transmission detector.

Preferably, the transmission detector is arranged in the same straight line with the beam output from the laser tube, and the detection pipeline is arranged between the transmission detector and the laser tube.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice; material, manufacturing, and assembly tolerances; and testing capability.

As used herein, the phrase at least one of A, B, and C should be construed to mean a logical (A OR B OR C), using a non-exclusive logical OR, and should not be construed to mean "at least one of A, at least one of B, and at least one of C."

The above-described embodiments are merely preferred embodiments of the present invention, and thus do not limit the scope of the present invention, and any insubstantial changes and substitutions made by those skilled in the art based on the present invention are intended to be within the scope of the present invention.

What is claimed is:

1. A fluid transparency detection method applying a detection device comprising:
   a detection pipeline which allows light beams to be incident on and emergent from a fluid in the detection pipeline;
   a laser tube used for outputting an incident light beam; and
   a photoelectric detector used for detecting an emergent light beam from the fluid, and comprising a scatter detector and a transmission detector,
   comprising steps of:
   S1: introducing pure fluid into the device, obtaining a scattered background noise value and a transmission background noise value of the device, and converting the scattered background noise value and the transmission background noise value correspondingly into a scattered light intensity background noise value $I_{scattered\ background\ noise}$ and a transmission light intensity background noise value $I_{transmission\ background\ noise}$;
   S2: introducing a fluid to be detected into the device, outputting a laser beam by the laser tube, respectively obtaining scattered light voltage signal and transmitted light voltage signal obtained by the scatter detector and the transmission detector, converting to obtain a scattered light intensity $I_{scatter}$ obtained by the scatter detector, a transmission light intensity $I_{transmission}$ obtained by the scatter detector, and a particle-absorbed light intensity $I_{absorb}$;
   S3: outputting a total laser light intensity $I_{total\ light\ intensity}$ according to the result obtained in S2, wherein the calculation formula of the total laser light intensity is as follows:

$$I_{total\ light\ intensity} = I_{scatter} + I_{transmission} + I_{absorb} - I_{scattered\ background\ noise} - I_{transmission\ background\ noise};\ \text{and}$$

S4: outputting a fluid transparency T according to the $I_{total\ light\ intensity}$ obtained in S3 and the $I_{transmission}$, wherein the calculation formula of the fluid transparency T is as follows:

$$T = (I_{transmission} - I_{transmission\ background\ noise}) / I_{total\ light\ intensity} \times 100\%.$$

2. The method according to claim 1, wherein the S3 further comprises a follow-up step of: repeating S2 and S3 to obtain a maximum value of the total laser light intensity $I_{max}$ in a time; and then the fluid transparency $T = (I_{transmission} - I_{transmission\ background\ noise})/I_{max} \times 100\%$.

3. The method according to claim 1, wherein the laser tube in S2 is movable.

4. The method according to claim 1, wherein the laser tube is moving during said detecting.

5. The method according to claim 1, wherein the laser tube is moving prior to said detecting.

6. The method according to claim 1, wherein the scatter detector is positioned out of a straight line with the beam output from the laser tube.

7. The method according to claim 6, wherein
   the scatter detector is arranged in a plane perpendicular to the beam output from the laser tube, and
   the scatter detector, the detection pipeline and the laser tube, with each as a vertex, form a right-angle shape.

8. The method according to claim 1, wherein the transmission detector is arranged in a same straight line with the beam output from the laser tube, and the detection pipeline is arranged between the transmission detector and the laser tube.

9. The method according to claim 1, wherein the detection device further comprises a drive unit for driving the laser tube to move.

10. The method according to claim 9, wherein the drive unit is an electric motor.

11. The method according to claim 9, wherein a movement range of the laser tube is diameter of cross section of the detection pipeline.

12. The method according to claim 8, wherein a movement of the laser tube is at a constant velocity.

13. The method according to claim 10, wherein a movement of the laser tube is a lead screw movement or a gear movement.

14. The method according to claim 1, wherein an optical axis of the scatter detector and an optical axis of the transmission detector are perpendicular to each other and intersect in the detection pipeline.

* * * * *